United States Patent [19]

Sebastian et al.

[11] Patent Number: 4,899,763
[45] Date of Patent: Feb. 13, 1990

[54] THERAPEUTIC APPLIANCE FOR THE WRIST

[75] Inventors: Peter R. Sebastian, Salisbury, Md.; Thomas V. Sebastian, Reading, Pa.

[73] Assignee: Safeguard Industrial Corporation, Leesport, Pa.

[21] Appl. No.: 254,748

[22] Filed: Oct. 7, 1988

[51] Int. Cl.$^4$ ............................................. A61F 13/00
[52] U.S. Cl. ...................... 128/878; 128/77; 128/87 R; 128/879; 128/DIG. 20
[58] Field of Search ............... 2/16, 20, 158, 159, 2/162; 128/77, 87 A, 87 R, 165, 878, 879

[56] References Cited

U.S. PATENT DOCUMENTS

| | | | |
|---|---|---|---|
| D. 259,955 | 7/1981 | Helferich | D24/64 |
| 1,469,315 | 10/1923 | Hansard | 273/189 |
| 2,823,668 | 2/1958 | Van Court et al. | 128/87 R |
| 3,164,841 | 1/1965 | Burtoff | 2/16 |
| 3,327,703 | 6/1967 | Gamm | 128/77 |
| 3,890,649 | 6/1975 | Diggins | 2/16 |
| 4,013,070 | 3/1977 | Harroff | 128/80 C |
| 4,441,490 | 4/1984 | Nirschl | 128/77 |
| 4,584,993 | 4/1986 | Nelson | 128/77 |

OTHER PUBLICATIONS

Advertisement, "Proflex Wrist Support", Comp Equipment Corp., St. Paul, Minn., 1985.
Advertisement brochure, "Viscolas", Steel Grip, Inc., Danville, Il., publication date unknown.

Primary Examiner—Richard J. Johnson
Assistant Examiner—Charles H. Sam
Attorney, Agent, or Firm—Wenderoth, Lind & Ponack

[57] ABSTRACT

A therapeutic appliance designed to provide support to the wrist and limit motion of the wrist to prevent repetitive movements of large amplitude felt to be a causative mechanism in injury to the median nerve within the carpal tunnel and other structures of this region. The appliance includes a series of interconnected air chambers aligned in parallel on the dorsal, lateral and medial surface of the device, a valve mechanism through which air is pumped into chambers by means of a handheld bulb, a semi-rigid non-metallic member on the dorsal surface of the device, and elastic strap closures on the volar surface of the device and an elastic strap wrapping around the thumb.

14 Claims, 6 Drawing Sheets

THERAPEUTIC APPLIANCE FOR THE WRIST

FIELD OF THE INVENTION

The present invention relates to a therapeutic appliance applied to the area of the wrist to treat and prevent injuries to the structures of this region.

BACKGROUND OF THE INVENTION

The wrist contains several structures that can be injured by repetitive large amplitude movements of the wrist. This includes the nerves of the region, particularly the median and ulnar nerves as well as tendons and the ligaments supporting the numerous bones of the wrist. A frequently utilized method of treatment is to provide a degree of immobilization to limit motion in the area and thus prevent further trauma to the injured structure of the area.

The prior art devices often achieve this goal by use of an entirely rigid device completely eliminating motion. Such devices if worn continuously can lead to local muscle atrophy from disuse, and can significantly impair finger motion needed in most activities of daily living. Rigid devices that entirely encompass the wrist can produce unwanted pressure and irritation over bony protuberances of the wrist and distal ends of the bones of the forearm. Nerves which lie in close proximity to the bones (ulnar and superficial radial nerves) can also be compressed/irritated by such devices.

Closure devices for most wrist splints consist of cumbersome series of laces or straps that can be difficult to apply particularly with the other free hand. Other problems encountered by such closures include compression of superficially located nerves (median) and particularly those lying in close proximity to underlying bones (ulnar and superficial radial nerves). Compression by tightly bound circumferential closures may also impair drainage of veins from the hand/wrist area.

SUMMARY OF THE INVENTION

The device of the present invention aims to avoid these aforementioned problems by utilizing a combination of interconnected air chambers aligned in parallel and running in a direction from the distal aspect of the forearm across the wrist and onto the hand. These chambers lie on the dorsal, medial and lateral aspect of the extremity being splinted. The chambers in combination with a semi-rigid plastic bar limited to the dorsal aspect of the device, supply the desired degree of therapeutic immobilization of the wrist. The semi-rigid nature of the device allows the degree of wrist extension necessary for maximal hand grip strength.

The use of air as a splinting mechanism allows it to conform to an individual wearers bony prominences with less chance of irritation. The degree of immobilization can be easily varied by adding or substituting air from the device. Gaps are intentionally left on the volar surface of the device to prevent pressure over the median nerve and draining veins on the surface of the wrist.

The device is closed around the wrist and hand by a series of neoprene elasticized material tabs. The neoprene is laminated to a fabric which adheres to a male VELCRO strip located at the other end of the bladder system. Those closures located on the volar side of the wrist are sized and shaped to allow for the acceptance as the forearm increases in circumference. An additional closure, made of the same material extends from the top edge of the three longest chambers forming a central section of the bladder system. This closure passes between the thumb and index finger and is cut in a manner to avoid rubbing the crease area therebetween. This strap moves across the thenar eminence of the palm and is attached to a strip of hooks of a hook and fastener attachment positioned in the vicinity of the volar surface of the wrist. The primary function of the closure is to maintain the proper position on the extremity.

The present invention thus provides a means of applying therapeutic immobilization of the wrist for the purposes of preventing injury to the neural, tendinous and ligamentous structure of the wrist caused by excessive repetitive motion. The device is composed of a semi-rigid plastic support limited to the dorsal surface, flanked on each side by a series of longitudinally extending, interconnected and parallel air chambers filled through a valve at the proximal end of the device. The air chambers and semi-rigid plastic support can optionally overlie an elastic glove-like lining facing the wrist from the inner surface of the appliance.

BRIEF SUMMARY OF THE DRAWINGS

The invention will now be described with reference to the accompanying drawings, in which.

DETAILED DESCRIPTION OF THE PREFERRED EMBODIMENTS

Figure 1:
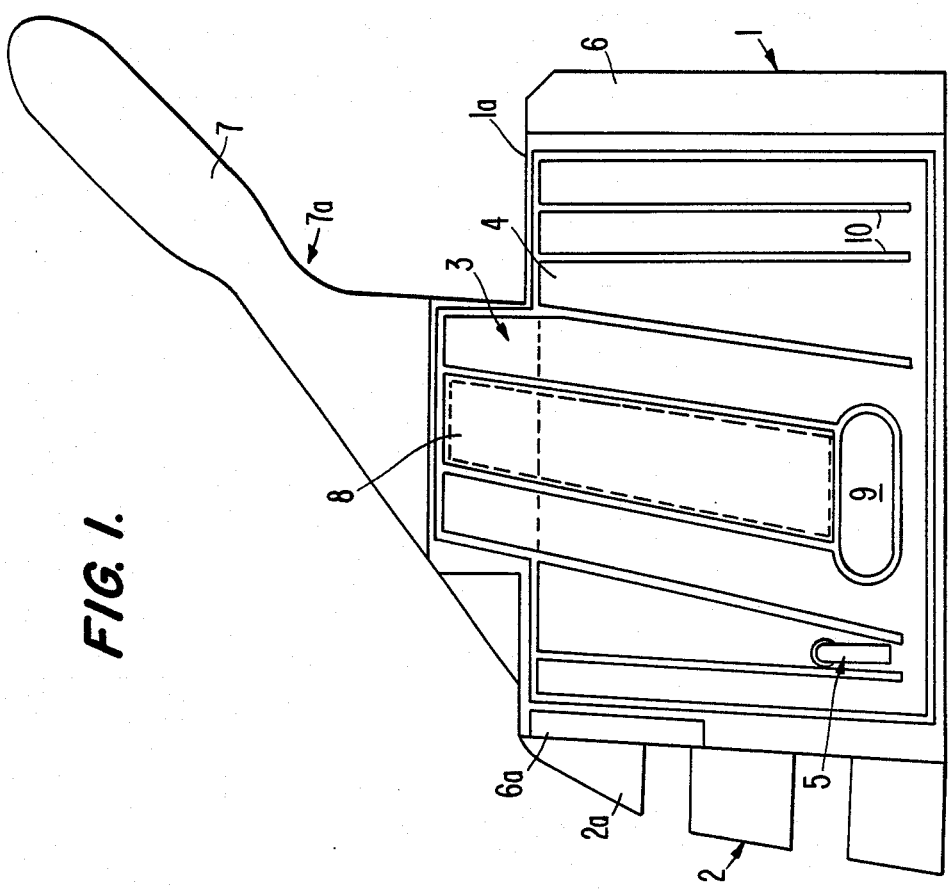
FIG. 1 is a top view of the appliance of the invention for a user's left hand.

The therapeutic appliance of the present invention provides support to a user's wrist and comprises a base 1 elongated in a longitudinal direction and having opposed ends spaced apart in the longitudinal direction; means 2 for removably attaching the ends of the base together such that the base can be positioned around a person's wrist; an air bladder 3 supported on the base, the air bladder having at least one air chamber 4 to provide support to the wrist when inflated; and air conduit means 5 for inflating the air bladder.

Figure 2:
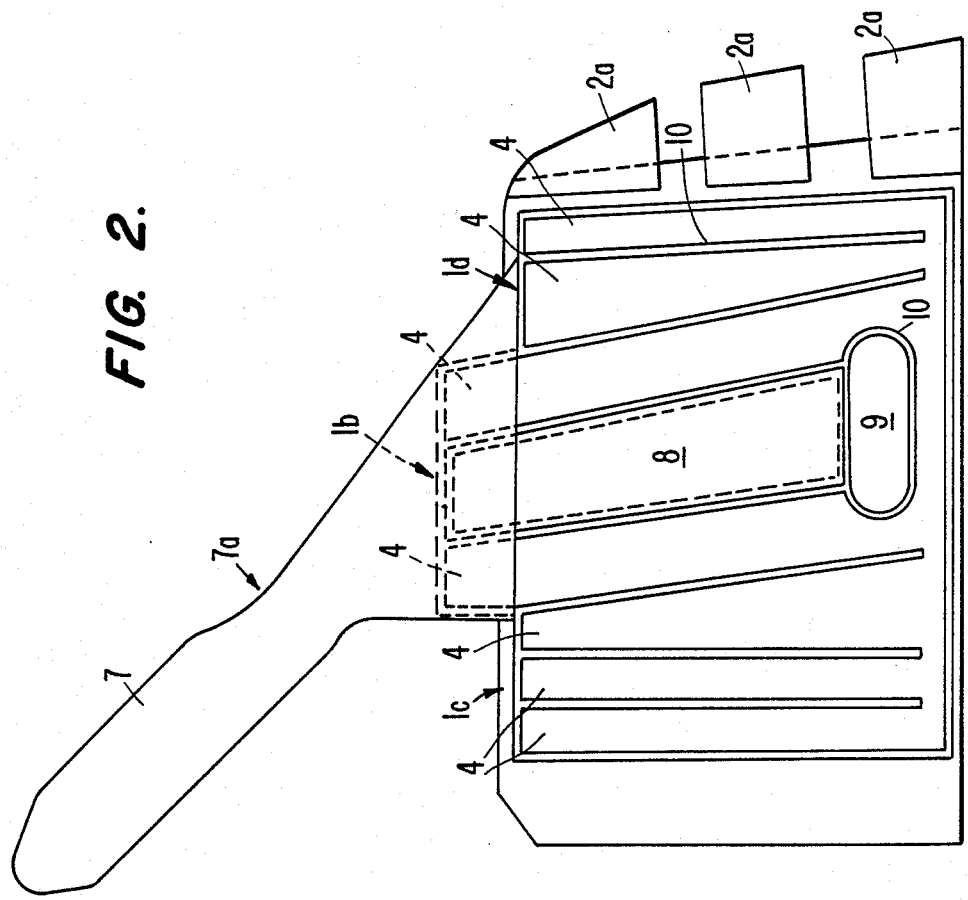
FIG. 2 is a bottom view of the appliance shown in FIG. 1.
Figure 3:
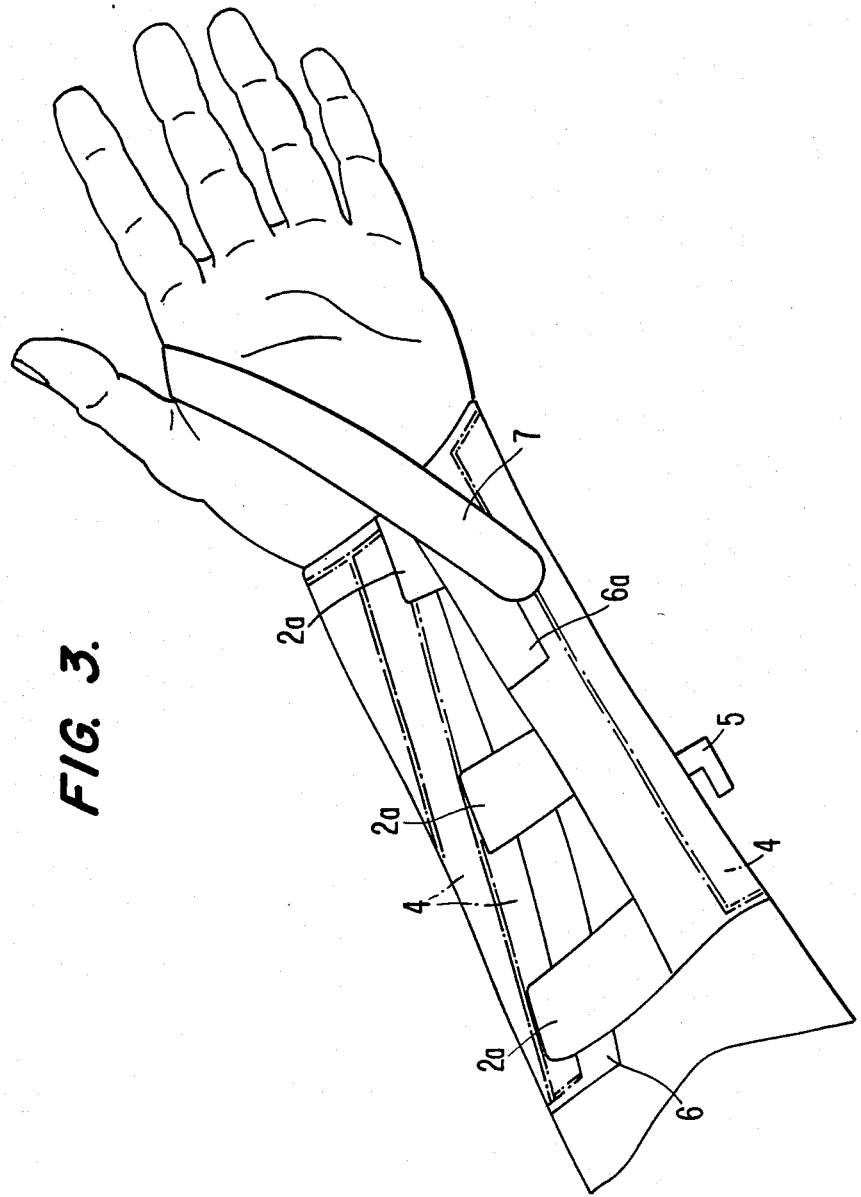
FIG. 3 is a perspective view of the appliance when in position on the left hand of a user.

The attaching means comprises at least one strap 2a fixed to one of the ends of the base and connection means 6 for removably attaching the strap to the other one of the ends of the base. Preferably, the attaching means comprises a plurality of spaced-apart straps 2a. For instance, as shown in FIGS. 1-3, the appliance can have three straps 2a. Another strap 7 which comprises a thumb/palm strap extends from a lateral edge 1a of the base extending between the ends of the base facing the fingers, the palm strap 7 having a length sufficient to extend over a back portion of a user's hand, between the thumb and index finger and over a portion of the palm. The appliance further includes connection means 6a for removably attaching a free end of the palm strap to a portion of the base located on the volar portion of the wrist when the appliance is positioned on the user's hand.

Figure 4:
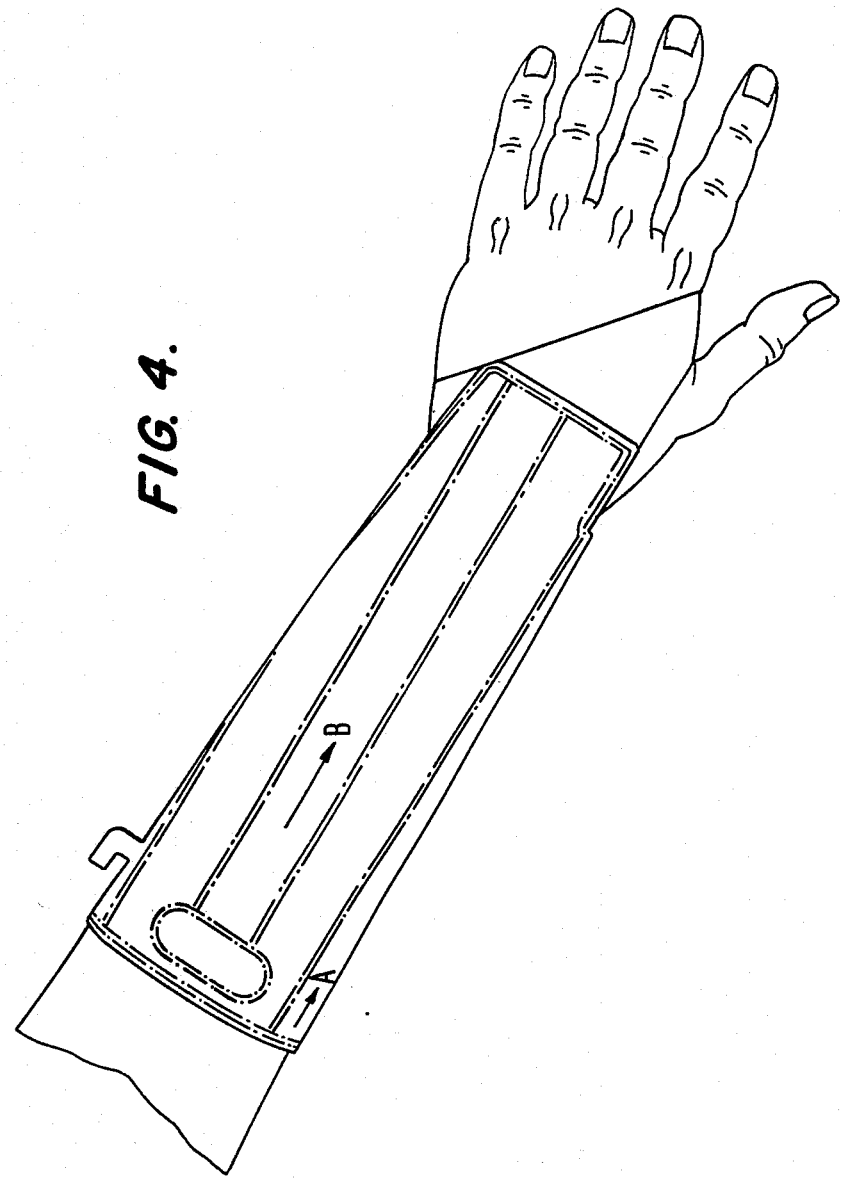
FIG. 4 is another perspective view of the appliance shown in FIG. 3.

The appliance can also include resilient means 8 supported on the base 1 for resisting bending of a user's wrist in a direction towards the dorsal surface of the wrist when the appliance is positioned on the user's hand, the resilient means comprising a non-metallic, flexible member which returns to its original shape after being elastically deformed. For instance, the flexible member can comprise a strip or bar of plastic material. The air bladder 3 preferably has a plurality of air chambers (which can be elongated or have any other desired configuration) in fluid communication with each other. As shown in FIGS. 1 and 2, a central section 1b of the base includes a plurality of air chambers 4 which are positioned to apply pressure against the dorsal surface of a user's wrist, a first end section 1c on one side of the central section includes a plurality of the air chambers 4 positioned to apply pressure against one side and an adjacent part of the volar surface of the wrist, and a second end section 1d on the other side of the central section includes a plurality of the air chambers 4 positioned to apply pressure against the other side and an adjacent part of the volar surface of the wrist such that none of the air chambers 4 are positioned to apply pressure against the median nerve of the hand. As shown in FIG. 3, the air chambers 4 located closest to the ends of the base 1 are spaced apart from each other when the appliance is in position on a user's hand and thus prevents pressure from being applied over the median nerve and avoids draining veins on the surface of the wrist. As shown in FIGS. 1 and 2, the air chambers are elongated in a direction substantially perpendicular to the longitudinal direction. However, the air chambers of the first and second end sections 1c, 1d are preferably elongated in a first direction substantially perpendicular to the longitudinal direction and the air chambers in the central section 1b are elongated in a second direction slightly inclined to the first direction, the second direction extending towards the fingers and away from the thumb when the appliance is positioned on a user's hand as shown in FIG. 4. The first direction is illustrated by arrow A and the second direction is illustrated by arrow B in FIG. 4. The angle between directions A and B is relatively small and on the order of a few degrees. The resilient means 8 is supported on the central section 1b of the base, and as shown in FIGS. 1 and 2, the flexible member is parallel to and positioned between two of the air chambers 4 of the central section 1b. Furthermore, a dead air space 9 which is not inflated can be provided at an end of the flexible member opposite to the edge of the base from which the palm strap 7 extends.

The air bladder 3 is configured such that it is generally straight along an edge thereof facing away from a user's fingers but the edge thereof facing the user's fingers is stepped such that the air chambers 4 in the central section 1b of the base are longer than those in the adjacent sections 1c and 1d. Furthermore, although the neoprene padded foam material of the palm strap 7 is triangular in shape at the portion thereof attached to the base 1 as shown in FIGS. 1 and 2, this section could be extended to cover part or all of the underside of the base 1. The hook and fastener attachment material of the connection means 6, 6a can entirely cover the sides of the straps 2a, 7 facing the surface of the hand when the appliance is positioned on a user's hand. Also, the hook and fastener attachment forming the connection means 6a can be extended between both edges of the base rather than extend part way from the edge facing the user's fingers as shown in FIG. 1.

The base 1 can comprises a first sheet of heat sealable material and the air bladder can comprise a second sheet of heat sealable material, the air chambers 4 being defined by heat seals 10 between the first and second sheets. Alternatively, the base can comprise a sheet of material and the bladder can comprise two sheets of heat sealable material supported on the base. the flexible member 8 is held between the two sheets of heat sealable material by providing a heat seal entirely therearound. Likewise, the dead air space 9 can be formed by a heat seal 10. The straps 2a and 7 are comprised of a stretchable padded foam material such as neoprene padded foam. The connection means 6, 7a can comprise hook and fastener attachments such as by providing loops (or other material which will securely engage hooks) on one side of the straps 2a, 7 and hooks provided at opposite ends of the base on one side thereof. For instance, as shown in FIG. 1, the hooks can be provided at the positions shown at 6a and 6. To provide more comfort in wearing the appliance, the straps 2a are fixed to the bottom side of the base 1 facing the hand as shown in FIG. 2. By providing a plurality of such straps 2a, the appliance can be flexed more when in position on a user's wrist and due to the gap created by the thickness of the straps 2a between the bottom of the base 1 and a user's wrist, heat and sweat can escape from the skin of the user. Furthermore, by providing the straps 2a extending from the bottom of the base of the appliance, such straps 2a do not interfere with the attachment of the palm strap 7 as shown in FIG. 3. Furthermore, to avoid irritation to the area between the thumb and index finger, the palm strp 7 is thinner at a position 7a where the palm strap passes between the thumb and index finger. The air conduit means 5 includes an air conduit having a valve at an outlet end thereof, the outlet end being adapted for connection to an air pump for filling the air chambers with air. Such an air pump can comprise a conventional squeeze bulb for pumping the air chambers.

Figure 5:
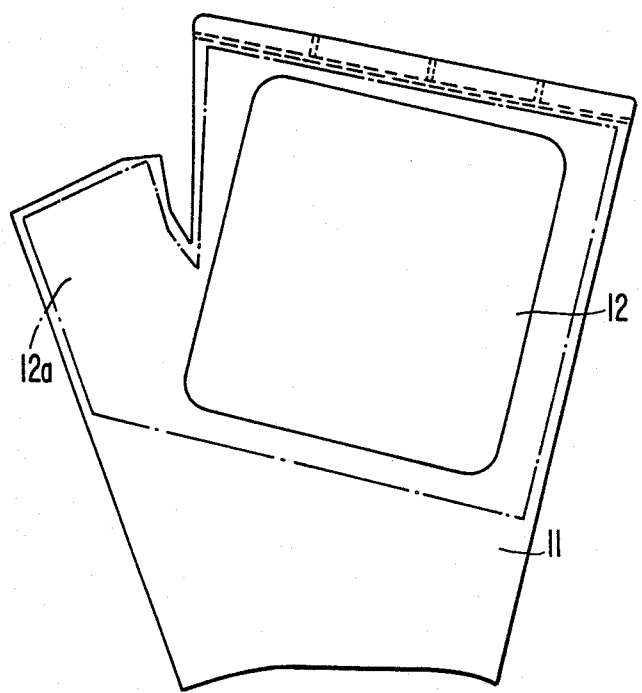
FIG. 5 is a perspective view of a glove for use with the appliance of the present invention.

The appliance of the present invention can be worn in combination with a glove 11 fitted under or over the appliance. The glove 11 can have pad means 12 as shown in FIG. 5 for absorbing vibration. The pad means can comprise a pad 12a which extends over the palm and up to the second joint of a user's fingers. Alternatively, the pad means 12 can be mounted on the dorsal surface of the glove 11 to protect the dorsal surface of the hand and fingers. Furthermore, the pad means 12 can be provided on the inside or outside of the glove 11.

To accomodate different wrist sizes, the number of air chambers can be increased or decreased or the sizes of the air chambers can be varied, e.g. the width of the air chambers may be varied between ⅛ to ⅜ of an inch. The material of the air bladder can have a Denier of about 210 in order to provide protection against penetration thereof. Furthermore, a glove can be worn over the appliance to provide protection when the appliance is worn in an industrial work environment.

In a further embodiment, not shown in the drawings, a plastic tube can be provided within the air chambers 4 to provide additional support in the appliance whether inflated or not.

Figure 6:
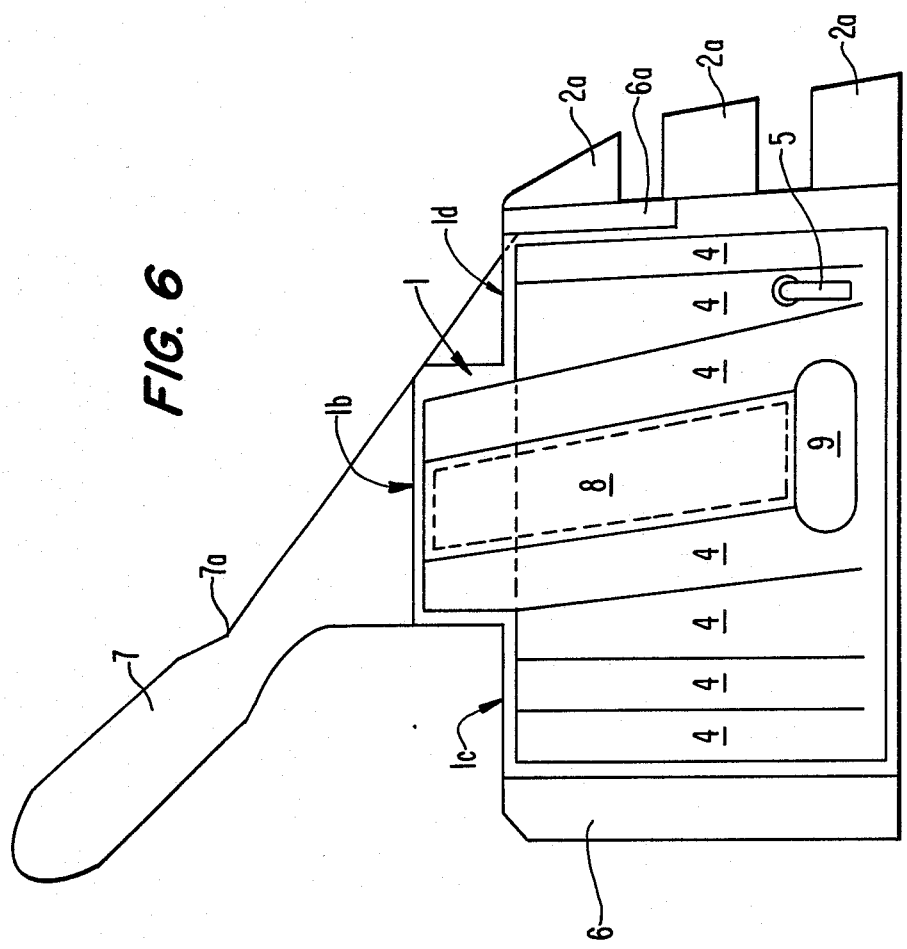
FIG. 6 is a top view of the appliance of the present invention for a user's right hand.

The appliance shown in FIGS. 1–4 is for a user's left hand. An appliance for a user's right hand is a mirror image of the appliance for the left hand, as shown in FIG. 6.

While the invention has been described with reference to the foregoing embodiments, many changes and variations may be made thereto which fall within the scope of the appended claims.

What is claimed is:

1. An appliance for providing therapeutic immobilization of a person's wrist, said appliance comprising:
   a base extending in a longitudinal direction and having opposed ends spaced apart in said longitudinal direction,
   said base of such a size as to be placed over a person's wrist;
   means for removably attaching said ends together such that the base can be positioned around a person's wrist;
   an air bladder supported on said base, said air bladder having opposed terminal ends spaced apart in said longitudinal direction and at least one air chamber to provide support to the wrist when said base is positioned around the wrist and said air bladder is inflated,
   each of said at least one air chamber being located on said base between said opposed terminal ends of said air bladder,
   said opposed terminal ends of said air bladder being spaced apart from one another a predetermined distance when said attaching means removably attaches said ends of said base together, said distance being such that the appliance is removably securable to the person's wrist in a position at which the air chambers of said air bladder do not cover the median nerve and avoid exerting pressure on the median nerve when said air bladder is inflated; and
   air conduit means communicating with said air bladder for allowing air to pass through said conduit means to said air bladder to inflate said air bladder.

2. The appliance of claim 1, wherein said attaching means comprises at least one strap fixed to one of said ends of said base and connection means for removably attaching said strap to the other one of said ends of said base.

3. The appliance of claim 1, wherein said attaching means comprises a plurality of spaced-apart straps fixed to one of said ends of said base and connection means for removably attaching each of said straps to the other one of said ends of said base.

4. The appliance of claim 1, wherein said base has a lateral edge extending between said ends of said base, and further comprising a palm strap having a free end and extending from said lateral edge of said base, said palm strap having a length sufficient to extend over a back portion of a person's hand, between the thumb and index finger and over a portion of the palm when the appliance is removably secured to the person's wrist in said position and connection means for removably attaching the free end of said palm strap to a portion of said base located on the volar portion of the wrist when the appliance is removably secured to the persons' wrist in said position.

5. The appliance of claim 1, further comprising resilient means supported on said base for resisting bending of a person's wrist in a direction towards the dorsal surface of the wrist when the appliance is removably secured to the person's wrist in said position, said resilient means comprising a non-metalic, flexible member which returns to its original shape after being elastically deformed.

6. The appliance of claim 1, wherein said at least one air chamber comprises a plurality of elongated air chambers in fluid communication with each other.

7. The appliance of claim 6, wherein said base has a central section, a first end section disposed to one side of said central section in said longitudinal direction, and a second end section disposed to the other side of said central section in said longitudinal direction, said central section of said base including a plurality of said air chambers which apply pressure against the dorsal surface of a person's wrist, said first end section including a plurality of said air chambers which apply pressure against one side and an adjacent part of the volar surface of the wrist, and said second end section including a plurality of said air chambers which apply pressure against the other side and an adjacent part of the volar surface of the wrist all when the appliance is removably secured to the person's wrist in said position.

8. The appliance of claim 7, wherein said air chambers are elongated in a direction substantially perpendicular to said longitudinal direction.

9. The appliance of claim 7, wherein said air chambers of said first and second sections of said base are elongated in a first direction substantially perpendicular to said longitudinal direction and said air chambers in said central section are elongated in a second direction slightly inclined to said first direction, said second direction extending towards the fingers and away from the thumb when the appliance is removably secured to the person's wrist in said position.

10. The appliance of claim 7, further comprising resilient means supported on said central section of said base for resisting bending of a person's wrist in a direction towards the dorsal surface of the wrist when the appliance is removably secured to the person's wrist in said position, said resilient means comprising a non-metallic, flexible member which returns to its original shape after being elastically deformed, said member being parallel to and positioned between two of said air chambers of said central section.

11. The appliance of claim 3, wherein said straps comprise stretchable padded foam material, said connection means comprise hook and fastener attachments, and the straps have one end thereof fixed to a side of the base facing the surface of a person's wrist when the appliance is removably secured to the person's wrist in said position to promote air circulation and allow heat and perspiration to escape from the skin of the person when the appliance is in use.

12. The appliance of claim 4, wherein said palm strap comprises a stretchable padded foam material having a configuration which is thinner at a position where said palm strap passes between the thumb and index finger.

13. The appliance of claim 1, wherein said base comprises a first sheet of heat sealable material and said air bladder comprises a second sheet of heat sealable material, said air chamber beingdefined by heat seals between said first and second sheets.

14. The appliance of claim 7, wherein said air conduit means includes an air conduit having an outlet end and a valve at outlet end thereof, said outlet end being adapted for connection to an air pump for filling said air chambers with air.

* * * * *